US008283472B2

(12) United States Patent
Haar, Jr. et al.

(10) Patent No.: US 8,283,472 B2
(45) Date of Patent: Oct. 9, 2012

(54) SYNTHESIS OF METHYLPHENIDATE AND ANALOGS THEREOF

(75) Inventors: Joseph P. Haar, Jr., Edwardsville, IL (US); Carl J. Schaefer, Crestwood, MO (US); Charles S. Kuivila, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 533 days.

(21) Appl. No.: 12/652,894

(22) Filed: Jan. 6, 2010

(65) Prior Publication Data
US 2010/0179327 A1 Jul. 15, 2010

Related U.S. Application Data

(60) Provisional application No. 61/143,431, filed on Jan. 9, 2009.

(51) Int. Cl.
*C07D 211/34* (2006.01)

(52) U.S. Cl. ........................................ 546/238

(58) Field of Classification Search ............ 546/238
See application file for complete search history.

(56) References Cited

U.S. PATENT DOCUMENTS

| 2,507,631 | A | 5/1950 | Hartmann et al. |
| 2004/0180928 | A1 | 9/2004 | Gutman et al. |
| 2006/0135777 | A1 | 6/2006 | Trafelet et al. |

OTHER PUBLICATIONS

Anzalone et al., "Syntheses and Equilibrations of 6- and 7-Carbomethoxy-trans-2-oxadecalins", J. Org. Chem., 1985, 50(15), pp. 2607-2612.
Byrne et al., "A Facile Porphyrin Esterification / Etherification Procedure", Tetrahedron Letters, 1988, 29(23), pp. 1421-1424.
Cohen et al., "Esterifiction of Carboxylic acids with Triethyl Orthoformate", Chemistry and Industry, 1965, pp. 349-350.
Ding et al., "Brain Kinetics of Methylphenidate (Ritalin) Enantiomers After Oral Administration", Synapse, 2004, 53, p. 168.
Heal et al., "Methylphenidate and its Isomers . . . ", CNS Drugs, 2006, 20, p. 713.
Oshima et al., "Enzymic Oxidative Coupling of Urushiol in Sap of the lac Tree, *Rhus vernicifera*", J. Org. Chem., 1985, 50, pp. 2613-2621.
Patrick et al., "Pharmacology of the enantiomers of *threo*-methylphenidate", J. Pharmacol Exp. Therap., 1986, 241, p. 152-158.
Portoghase et al., "Relative Hydrolytic Rates of Certain Alkyl . . . ", J. Pharm. Sci., 1961, 50, pp. 494-501.
Trujillo et al., "Facile Esterfication of Sulfonic Acids and Carboxylic Acids with Triethylorthoacetate", Tetrahedron letters, 34 (46), 1993, pp. 7355-7358.
Zhang et al., "Facile Sunthesis of N-protected Amino Acid Esters Assisted by Microwave Irradiation", Int. J. Pept. Res. Ther., 2008, 14, pp. 219-222.
Prashad et al., "Enzymatic resolution of (+/−)-threo-methylphenidate", Tetrahedron Asymmetry, 9(12), 1998, pp. 2133-2136, XP 004131327.
Deutsch et al., "Synthesis and Pharmamology of Potential Cocaine Antagonists. 2. Structure-activity Relationship Studies of Aromatic Ring-Substituted methylphenidate Analogs", Journal of Medicinal Chemistry, American chemical Society, 39(15), 1996, pp. 1201-1209, XP 000602079.

*Primary Examiner* — Gordon R Baldwin
*Assistant Examiner* — Ana Muresan

(57) ABSTRACT

A synthetic process for the preparation of amino acid esters such as methylphenidate and analogs thereof is disclosed. The process involves reacting an amino acid such as α-phenyl-α-(2-piperidinyl)acetic acid or an analog thereof with an alcohol such as methanol in the presence of an acid and a water sequestrant such as trimethyl orthoacetate. In some embodiments, the water sequestrant is added to the reaction mixture after an initial period of esterification and then the reaction is allowed to continue. The α-phenyl-α-(2-piperidinyl)acetic acid methyl ester or analog thereof is then isolated from the reaction mixture. In one variation of the process, the supernatant liquid may be recycled in subsequent runs to increase yield and product purity.

20 Claims, No Drawings

SYNTHESIS OF METHYLPHENIDATE AND ANALOGS THEREOF

CROSS REFERENCE TO RELATED APPLICATIONS

This application claims the benefit of U.S. Provisional Application No. 61/143,431 filed Jan. 9, 2009, which is incorporated herein in its entirety.

FIELD

The present invention relates to processes for esterification of amino acids with alcohols, acids and water sequestrants, and in particular, esterification of ritalinic acid with alcohols, acids and water sequestrants. The process may be used to prepare threo-methylphenidate and its analogs from the corresponding amino acid and methyl alcohol in the presence of an orthoester as the water sequestrant.

INTRODUCTION

Methylphenidate has been reported to be effective in the treatment of central nervous system disorders such as attention deficit disorder and attention deficit hyperactivity disorder (Pelham et al., *Arch. Gen. Psych.* 42:948, 1985; Spencer, *J. Am. Acad. Child & Adoles. Psych.* 35:409, 1996). The biologically active form of methylphenidate is the threo-ester, i.e. threo-methylphenidate or threo-α-phenyl-α-(2-piperidinyl)acetic acid methyl ester. Threo-methylphenidate is generally used therapeutically as a racemic mixture containing the d- and l-forms of which the d-enantiomer, i.e. d-threo methylphenidate, is the more active form (Patrick, *J. Pharmacol. Exp. Therap.* 241:152, 1987; Ding et al., *Synapse* 53:168, 2004; Heal et al., *CNS Drugs* 20:713, 2006).

Processes for the synthesis of methylphenidate have been reported (see, for example, U.S. Pat. Nos. 2,507,631 and 2,957,880; Portoghese et al., *J. Pharm. Sci.* 50:494-501, 1961). More recently, processes for synthesis of threo-methylphenidate and its d-enantiomer have been reported (see, for example, U.S. Patent Application Publication No. 20060135777). Nevertheless, there remains a continuing need for new and efficient synthetic processes for the production of methylphenidate and its analogs.

SUMMARY

Accordingly, the inventors herein have succeeded in devising a new synthetic process for the production of amino acid esters such as methylphenidate and its analogs. The process involves reacting an amino acid such as α-phenyl-α-(2-piperidinyl)acetic acid with an alcohol such as methanol in the presence of an acid, and in various embodiments, a water sequestrant. The water sequestrant effectively removes water from the reaction mixture and it may be added in the starting reaction mixture or after the esterification process has proceeded to some extent.

Thus, in various embodiments, the present invention involves a synthetic esterification process. The process includes providing an amino acid of Formula I:

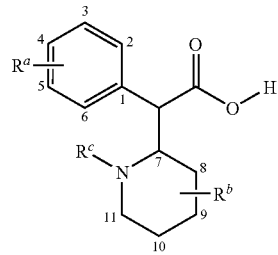

Formula I wherein $R^a$ can be a substituent at one or more of carbons 2, 3, 4, 5 and 6 of the phenyl ring, wherein the substituent may independently be hydrogen, alkyl, alkoxy, haloalkyl, haloalkoxy, hydroxyalkyl, alkoxyalkyl, halogen and —$NR_m R_n$, wherein $R_m$ and $R_n$ may independently be hydrogen, alkyl, haloalkyl and alkoxyalkyl. $R^b$ in Formula I above may be a substituent at one or more of carbons 7, 8, 9, 10 and 11 of the piperidine ring, wherein the substituent may independently be hydrogen, oxo, alkyl, alkoxy, haloalkyl, haloalkoxy, hydroxyalkyl, alkoxyalkyl and halogen. $R^c$ in Formula I above may be hydrogen, alkyl, haloalkyl, aralkyl, cycloalkylalkyl, hydroxyalkyl, alkoxyalkyl, and

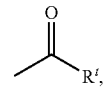

wherein $R^t$ may be alkyl, alkoxy, cycloalkyl, cycloalkylalkyl, aralalkoxy and aralkyl.

Still referring to the synthetic esterification process above, the reaction mixture further includes an alcohol and an acid. The alcohol may be of formula $R^y$—OH, wherein $R^y$ may be alkyl, haloalkyl, cycloalkyl, cycloalkylalkyl, aryl, aralkyl, heteroaryl, and heteroaralkyl. The acid may be methanesulfonic acid, p-toluenesulfonic acid, hydrochloric acid, hydrobromic acid, sulfuric acid, and phosphoric acid. The reaction mixture including the amino acid, alcohol and acid is then contacted with a water sequestrant to produce a reaction mixture containing an amino acid ester of Formula II:

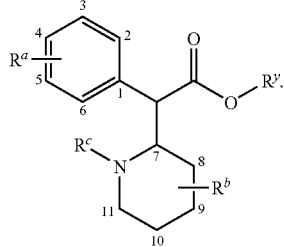

Formula II

The compound of Formula II may then be isolated from the reaction mixture. In various embodiments, the amino acid of Formula I may be ritalinic acid. In other embodiments, the amino acid ester of Formula II may be threo-α-phenyl-α-(2-piperidinyl)acetic acid methyl ester. For instance, the process may include reacting threo-α-phenyl-α-(2-piperidinyl)acetic acid with methanol in the presence of a water sequestrant and an acid, and isolating the threo-α-phenyl-α-(2-piperidinyl) acetic acid methyl ester or a pharmaceutically acceptable salt thereof.

In various embodiments, the water sequestrant referred to above may be an orthoester of the formula $R^xC(OR^y)_3$, wherein $R^x$ is hydrogen or alkyl, and $R^y$ is as previously defined for Formula I. For instance, the orthoester may be $CH_3C(OCH_3)_3$. In certain embodiments, the water sequestrant may be employed in an amount from about 0.5 to about 4 molar equivalents to that of the amino acid. In various embodiments, the alcohol may be methanol. In yet another embodiment, the reaction may be carried out with an amount of alcohol from about 0.5 to about 1000 molar equivalents to that of the amino acid of Formula I, and in various embodiments, from about 5 to about 50 molar equivalents to that of the amino acid of Formula I.

In another embodiment, the acid may be methanesulfonic acid, p-toluenesulfonic acid, hydrochloric acid, hydrobromic acid, sulfuric acid, and phosphoric acid. The acid may be employed in the synthetic esterification process in an amount from about 0.5 to about 4 molar equivalents to that of the amino acid of Formula I as defined above.

In another embodiment, the reaction may be carried out from about 0° C. to about 200° C. for about 0.2 to about 50 hours, for instance from about 25° C. to about 150° C. for about 0.5 to about 25 hours, and in another instance from about 50° C. to about 100° C. for about 3 to about 20 hours.

In yet another embodiment, the synthetic esterification process can comprise reacting, in a mixture, an amino acid of Formula I as defined above with an alcohol as defined above in the presence of an acid to produce a reaction mixture containing an amino acid ester of Formula II as defined above, then contacting the reaction mixture with a water sequestrant prior to complete conversion to the amino acid ester of Formula II, then allowing the reaction to continue to produce the amino acid ester of Formula II, and then isolating the amino acid ester of Formula II or a pharmaceutically acceptable salt thereof. In various embodiments, the reaction may continue after contacting the reaction mixture with a water sequestrant and may be carried out from about 50° C. to about 100° C. for about 3 to about 6 hours. In yet another embodiment, the isolating can include precipitating or crystallizing the amino acid ester of Formula II or a pharmaceutically acceptable salt thereof from the mixture. The reaction may further include capturing supernatant remaining after precipitating or crystallizing the amino acid ester of Formula II or a pharmaceutically acceptable salt thereof, and repeating the above actions one or more times utilizing captured supernatant.

In yet another embodiment, a process is provided for preparing threo-α-phenyl-α-(2-piperidinyl)acetic acid methyl ester that includes reacting, in a mixture, threo-α-phenyl-α-(2-piperidinyl)acetic acid with methanol in the presence of an acid; (ii) contacting the reaction mixture with a water sequestrant prior to complete conversion to threo-α-phenyl-α-(2-piperidinyl)acetic acid methyl ester; (iii) allowing the reaction to continue to produce threo-α-phenyl-α-(2-piperidinyl) acetic acid methyl ester; and (iv) isolating threo-α-phenyl-α-(2-piperidinyl)acetic acid methyl ester or a pharmaceutically acceptable salt thereof. In various embodiments, the reaction may continue after contacting the reaction mixture with a water sequestrant and may be carried out from about 50° C. to about 100° C. for about 3 to about 6 hours. In yet another embodiment, the isolating can include precipitating or crystallizing the threo-α-phenyl-α-(2-piperidinyl)acetic acid methyl ester or a pharmaceutically acceptable salt thereof from the mixture. The reaction may further include capturing supernatant remaining after precipitating or crystallizing the threo-α-phenyl-α-(2-piperidinyl)acetic acid methyl ester or a pharmaceutically acceptable salt thereof, and repeating the above actions one or more times utilizing captured supernatant.

DETAILED DESCRIPTION

Abbreviations and Definitions

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

n the written descriptions of molecules and substituents, molecular descriptors can be combined to produce words or phrases that describe substituents. Such descriptors are used in this document. Examples include such terms as aralkyl (or arylalkyl), heteroaralkyl, heterocycloalkyl, cycloalkylalkyl, aralkoxyalkoxycarbonyl and the like. A specific example of a compound encompassed with the latter descriptor aralkoxyalkoxycarbonyl is $C_6H_5$—$CH_2$—$CH_2$—O—$CH_2$—O—C(O)— to wherein $C_6H_5$— is phenyl. It is also to be noted that a substituents can have more than one descriptive word or phrase in the art, for example, heteroaryloxyalkylcarbonyl can also be termed heteroaryloxyalkanoyl. Such combinations are used herein in the description of the compounds and methods of this invention and further examples are described herein.

Threo-ester: The terms "threo-ester", "threo-methylphenidate" and "threo-methylphenidate analogs" as well as their corresponding acids as used herein, include the d,l-threo-racemic mixtures, the d-threo-enantiomers and/or the l-threo-enantiomers. Further, reference herein to threo-esters, threo-methylphenidate and threo-methylphenidate analogs is also intended to include pharmaceutically acceptable salts of the named compounds. For example, reference to threo-methylphenidate is intended to include the hydrochloride salt of threo-methylphenidate.

Analog: The term "analog" as used herein refers to a compound in which one or more atoms are replaced with a different atom or group of atoms.

Aromatic: The term "aromatic" as used herein, alone or as part of a group of atoms, denotes optionally substituted homo- or heterocyclic aromatic groups. These aromatic groups are preferably monocyclic, bicyclic, or tricyclic groups containing from 6 to 14 atoms in the ring portion. The term "aromatic" can apply to the "aryl" and "heteroaryl" substituents defined herein.

Alkaryl: The terms "alkaryl" or "alkylaryl" as used herein describe substituents, which are preferably aryl groups, having a lower alkyl substituent such as toluoyl, ethylphenyl, or methylnapthyl.

Alkoxy: The term "alkoxy", alone or in combination with other terms herein, means an alkyl ether substituent, wherein the term alkyl is as defined herein. Examples of alkoxy substituents include methoxy, ethoxy, n-propoxy, isopropoxy, n-butoxy, iso-butoxy, sec-butoxy, and tert-butoxy.

Alkoxyalkyl: The term "alkoxyalkyl" as used herein refers to an alkyl substituent, as defined herein, wherein one or more hydrogens of the alkyl are replaced with an alkoxy substituent.

Alkyl: The term "alkyl" as used herein describes substituents which are preferably lower alkyl containing from one to eight carbon atoms in the principal chain and up to about 20 carbon atoms. The principal chain may be straight or branched chain or cyclic and include methyl, ethyl, propyl, isopropyl, butyl, hexyl and the like.

Aralkyl: The term "aralkyl" as used herein describes substituents which are preferably lower alkyl containing from one to eight carbon atoms having an aryl substituent, such as benzyl, phenylethyl, or 2-napthylmethyl.

Aryl: The term "aryl" as used herein, alone or as part of a group of atoms, denotes optionally substituted homocyclic aromatic substituents, preferably monocyclic or bicyclic substituents containing from 6 to 12 carbons in the ring portion, such as phenyl, biphenyl, naphthyl, substituted phenyl, substituted biphenyl or substituted naphthyl.

Cycloalkyl: The term "cycloalkyl", alone or as part of a group of atoms, means a cyclic alkyl containing from 3 to about 10, preferably from 3 to about 8, and most preferably from 3 to about 6, carbon atoms. Examples of cycloalkyl include, but are not limited to, cyclopropyl, cyclobutyl, cyclopentyl, cyclohexyl, cycloheptyl, cyclooctyl, and perhydronaphthyl.

Cycloalkylalkyl: The term "cycloalkylalkyl" means an alkyl substituent as defined above that is substituted by a cycloalkyl substituent containing 3 to about 8, preferably 3 to about 6, carbon atoms. Examples of such cycloalkyl substituents include cyclopropyl, cyclobutyl, cyclopentyl, cyclohexyl and the like. A heterocyclic (heterocyclo) or heterocyclo portion of a heterocyclocarbonyl, heterocyclooxycarbonyl, heterocycloalkoxycarbonyl, or heterocycloalkyl group or the like is a saturated or partially unsaturated monocyclic, bicyclic or tricyclic heterocycle that contains one or more heteroatoms selected from nitrogen, oxygen and sulphur. Such a moiety can be optionally substituted on one or more ring carbon atoms by halogen, alkyl, alkoxy, oxo, and the like, and/or on a secondary nitrogen atom (i.e., —NH—) of the ring by alkyl, aralkoxycarbonyl, alkanoyl, aryl or aralkyl or on a tertiary nitrogen atom (i.e., =N—) by oxido and that is attached via a carbon atom. The tertiary nitrogen atom with three substituents can also attached to form an N-oxide (i.e., =N(O)—).

Haloalkyl: The term "haloalkyl" means an alkyl substituent as defined herein, wherein one or more hydrogens are replaced with a halogen. Examples of such haloalkyl substituents include chloromethyl, 1-bromoethyl, fluoromethyl, difluoromethyl, trifluoromethyl, 1,1,1-trifluoroethyl and the like.

Haloalkoxy: The term "haloalkoxy" denotes a haloalkyl, as defined herein, that is directly attached to an oxygen to form trifluoromethoxy, pentafluoroethoxy and the like.

Halogen: The terms "halogen" or "halo" as used herein, alone or as part of a group of atoms, refer to chlorine, bromine, fluorine, and iodine.

Heteroaralkyl: The term "heteroaralkyl" refers to an alkyl substituent as defined herein that is substituted by a heteroaryl substituent.

Heteroaryl: The term "heteroaryl" as used herein, alone or as part of a group of atoms, denotes optionally substituted aromatic groups having at least one heteroatom in at least one ring, and preferably 5 or 6 atoms in each ring. The heteroaryl group preferably has 1 or 2 oxygen atoms and/or 1 to 4 nitrogen atoms in the ring, and is bonded to the remainder of the molecule through a carbon. Exemplary heteroaryls include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl and the like. Exemplary heteroaryl substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

Heteroatom: The term "heteroatom" shall mean an atom other than carbon and hydrogen.

Heterocyclo: The terms "heterocyclo" or "heterocyclic" as used herein, alone or as part of a group of atoms, denote optionally substituted, and/or fully saturated or unsaturated, and/or monocyclic or bicyclic, and/or aromatic or non-aromatic groups having at least one heteroatom in at least one ring, and preferably 5 or 6 atoms in each ring. The heterocyclo substituent preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described below. Exemplary substituents include one or more of the following groups: hydrocarbyl, substituted hydrocarbyl, hydroxy, protected hydroxy, acyl, acyloxy, alkoxy, alkenoxy, alkynoxy, aryloxy, halogen, amido, amino, cyano, ketals, acetals, esters and ethers.

Hydroxyalkyl: The term "hydroxyalkyl" as used herein refers to an alkyl substituent, as defined herein, wherein one or more hydrogens are replaced with an —OH group.

Hydroxyl: The term "hydroxyl", alone or in combination, means a —OH group.

Oxo: The term "oxo" or "carbonyl", alone or as part of a group of atoms, means a —C(O)— group wherein the remaining two bonds (valences) can be independently substituted. The term carbonyl is also intended to encompass a hydrated carbonyl group —C(OH)$_2$—.

Pharmaceutically acceptable: The terms "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The terms "pharmaceutically acceptable salt" as used herein refer to acid addition salts or base addition salts of the compounds in the present disclosure. A pharmaceutically acceptable salt is any salt which retains the activity of the parent compound and does not impart any deleterious or undesirable effect on a subject to whom it is administered and in the context in which it is administered. Pharmaceutically acceptable salts include, but are not limited to, metal complexes and salts of both inorganic and carboxylic acids. Pharmaceutically acceptable salts also include metal salts such as aluminum, calcium, iron, magnesium, manganese and complex salts. In addition, pharmaceutically acceptable salts include, but are not limited to, acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, citric, edetic, edisylic, estolic, esyl, esylic, formic, fumaric, gluceptic, gluconic, glutamic, glycolic, glycolylarsanilic, hexamic, hexylresorcjnoic, hydrabamic, hydrobromic, hydrochloric, hydrolodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanlic, sulfonic, sulfuric, tannic, tartaric, teoclic, toluenesulfonic, and the like. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zürich, 2002; Berge et al., *J. Pharm. Sci.* 66: 1, 1977).

Pharmaceutically acceptable carrier: The terms "pharmaceutically acceptable carrier" as used herein refers to an excipient, diluent, preservative, solubilizer, emulsifier, adjuvant, and/or vehicle with which a compound is administered. Such carriers may be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when a compound is administered intravenously. Saline solutions and aqueous dextrose and glycerol solutions may also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A compound, if desired, may also combine minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compounds in combination with carriers are known to those of skill in the art.

Esterification Process

The present invention includes a synthetic process for the preparation of amino acid esters, such as threo-α-phenyl-α-(2-piperidinyl)acetic acid methyl ester, and analogs thereof. The process involves reacting an amino acid, such as α-phenyl-α-(2-piperidinyl)acetic acid, with an alcohol such as methanol in the presence of an acid, and a water sequestrant to remove water from the reaction mixture. The water sequestrant may be added in the starting reaction mixture or after the esterification process has proceeded to some extent and the process allowed to continue thereafter.

In accordance with the present invention, the amino acid and amino acid ester may be represented by Formulas I and II respectively;

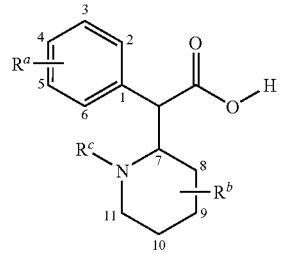

Formula I

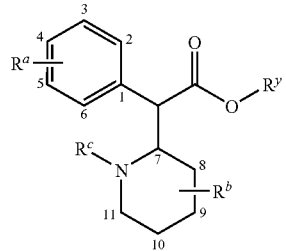

Formula II wherein $R^a$ is a substituent at one or more of carbons 2, 3, 4, 5 and 6 of the phenyl ring, wherein the substituent is independently selected from the group consisting of hydrogen, alkyl, alkoxy, haloalkyl, haloalkoxy, hydroxyalkyl, alkoxyalkyl, halogen and —$NR_mR_n$, wherein $R_m$ and $R_n$ are independently selected from the group consisting of hydrogen, alkyl, haloalkyl and alkoxyalkyl; wherein $R^b$ is a substituent at one or more of carbons 8, 9, 10 and 11 of the piperidine ring, wherein the substituent is independently selected from the group consisting of hydrogen, oxo, alkyl, alkoxy, haloalkyl, haloalkoxy, hydroxyalkyl, alkoxyalkyl and halogen; and wherein $R^c$ is selected from the group consisting of hydrogen, alkyl, haloalkyl, aralkyl, cycloalkylalkyl, hydroxyalkyl, alkoxyalkyl, and

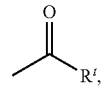

wherein $R^t$ is selected from the group consisting of alkyl, alkoxy, cycloalkyl, cycloalkylalkyl, aralalkoxy and aralkyl.

The process of the present invention includes, in various embodiments, reacting the amino acid with an alcohol in the presence of an acid and a water sequestrant. The alcohol may be any alcohol and, in particular, an alcohol characterized by the formula $R^y$—OH in which $R^y$ can be alkyl, haloalkyl, cycloalkyl, cycloalkylalkyl, aryl, aralkyl, heteroaryl, and heteroaralkyl. An excess amount of the alcohol is typically used in the reaction, for example, in an amount ranging from about 0.5 to about 1000 molar equivalents, and in particular about 5 to about 50 molar equivalents, compared to the amount of amino acid in the reaction mixture.

In some aspects, the reaction mixture may include an additional non-reactive solvent. The term "non-reactive solvent" refers to a solvent that does not chemically interfere with the reaction. Examples may include hexane, toluene, diethyl ether, chloroform, 1,4-dioxane, dimethylformamide, dimethyl sulfoxide, and dichloromethane.

The acid may be an organic acid or an inorganic acid. Such acids may include organosulfonic acids such as methanesulfonic and p-toluenesulfonic acids and the like. Inorganic acids may include sulfuric acid ($H_2SO_4$) and phosphoric acid ($H_3PO_4$), as well as hydrohalic acids such as hydrogen chloride (HCl), hydrogen bromide (HBO, and the like. Those skilled in the art will recognize these and other analogous acids capable of catalyzing the esterification reaction, but not chemically interfere with the reaction. Such acids may have a $pK_a$ less than 6, and in some embodiments a $pK_a$ less than 3, and in other embodiments a $pK_a$ less than zero. The amount of acid used is typically in a range of from about 0.5 to about 4 molar equivalents compared to the amount of amino acid in the reaction mixture.

The water sequestrant effectively removes water from the reaction mixture and suitable water sequestrants may include substances such as a water scavenger, a chemical process that consumes water, and the like. In some embodiments, the water sequestrant may be an orthoester of the formula $R^xC(OR^y)_3$ in which $R^x$ may be hydrogen or alkyl and $R^y$ may be alkyl, alkoxy, cycloalkyl, cycloalkylalkyl, aralalkoxy or aralkyl.

In some embodiments, the water sequestrant may be present in the starting reaction mixture. In other embodiments, the water sequestrant may be added after the reaction is allowed to proceed to produce at least some amino acid ester, but prior to complete conversion of the acid to the ester. The reaction is then continued in the presence of the water sequestrant. In some embodiments of such two-stage processes, the first stage of the reaction may be allowed to approach equilibrium such that a relatively stable amount of amino acid ester is present in the reaction mixture prior to addition of the water sequestrant. This may be determined upon taking successive samples from the reaction mixture over a period of time. The two stage process may advantageously improve yield and/or purity of the product ultimately recovered from the process.

In certain embodiments of the process in which the water sequestrant is present in the initial reaction mixture, the reaction conditions may include reacting at a temperature of from about 0° C. to about 200° C. for about 0.2 to about 50 hours, and in some embodiments from about 25° C. to about 150° C. for about 0.5 to about 25 hours, and in yet other embodiments from about 50° C. to about 100° C. for a period of from about 3 to about 20 hours. In embodiments involving a two-stage process, the initial reaction conditions prior to addition of the water sequestrant may include reacting at a temperature of from about 0° C. to about 200° C. for about 0.2 to about 50 hours, and in some embodiments from about 25° C. to about 150° C. for about 0.5 to about 25 hours, and in yet other embodiments from about 50° C. to about 100° C. for a period of from about 3 to about 20 hours. This may be followed during the second stage of the reaction in which the water sequestrant is present, by reacting at a temperature of from about 0° C. to about 200° C. for about 0.2 to about 50 hours, and in some embodiments from about 25° C. to about 150° C. for about 0.5 to about 25 hours, and in yet other embodiments from about 50° C. to about 100° C. for a period of from about 3 to about 20 hours, and in yet another embodiment from about 50° C. to about 100° C. for a period of from about 3 to about 6 hours, in the presence of the water sequestrant.

Following the esterification process, the amino acid ester may be isolated from the reaction mixture. In some embodiments, isolation of the amino acid ester may involve precipitation or crystallization of the amino acid ester. This may be achieved by any method known in the art such as, for example, by cooling the reaction mixture to precipitate the amino acid ester or by adding a solvent in which the amino acid ester is less soluble than the reaction mixture or by solvent exchange with a solvent in which the amino acid ester is less soluble. Further steps of purification may also be performed.

In some embodiments, the residual liquid remaining after precipitation of the amino acid ester, i.e., the supernatant, may be further used in one or more subsequent runs of the process. Thus, supernatant recovered from a first run of the process may be used in a second run of the process upon combining the supernatant with amino acid, alcohol, acid and, in some instances, a water scavenger. Accordingly, the supernatant from one or more runs of the process may be used in succeeding runs. This may result in a greater yield of the amino acid ester, a higher purity of the amino acid ester and/or a more efficient usage of reaction components.

In some embodiments, the present invention may be characterized as a process for preparing an amino acid ester, and in particular a threo-α-phenyl-α-(2-piperidinyl)acetic acid methyl ester, or analogs thereof. The process may include reacting threo-α-phenyl-α-(2-piperidinyl)acetic acid or an appropriate analog thereof with methanol in the presence of an acid and a water sequestrant such as described above. The threo-α-phenyl-α-(2-piperidinyl)acetic acid methyl ester or analog thereof, may then be isolated from the reaction mixture.

In certain embodiments the terms "threo-α-phenyl-α-(2-piperidinyl)acetic acid or an analog thereof" may be synonymous with the terms "amino acid of Formula I" and the terms "threo-α-phenyl-α-(2-piperidinyl)acetic acid methyl ester or an analog thereof" may be synonymous with the terms "amino acid esters of Formula II" as described above. In other embodiments, compounds characterized as a threo-α-phenyl-α-(2-piperidinyl)acetic acid or an analog thereof may be a subset of the amino acids of Formula I and, similarly, compounds characterized as a threo-α-phenyl-α-(2-piperidinyl)acetic acid methyl ester or an analog thereof may be a subset of the amino acid esters of Formula II. In still other embodiments, compounds characterized as a threo-α-phenyl-α-(2-piperidinyl)acetic acid or an analog thereof may be a set of compounds that overlaps with the set of threo-acids of Formula I and, similarly, compounds characterized as a threo-α-phenyl-α-(2-piperidinyl)acetic acid methyl ester or an analog thereof may be a set of compounds that overlaps with the set of amino acid esters of Formula II.

In certain embodiments, the process may involve reacting in a mixture, threo-α-phenyl-α-(2-piperidinyl)acetic acid or analog thereof with methanol in the presence of an acid such as described above. The reaction is allowed to proceed and, prior to complete conversion to the threo-α-phenyl-α-(2-piperidinyl)acetic acid methyl ester or analog thereof, the reaction mixture is contacted with a water sequestrant. The reaction is then allowed to proceed to continue to produce threo-α-phenyl-α-(2-piperidinyl)acetic acid methyl ester or analog thereof. The threo-α-phenyl-α-(2-piperidinyl)acetic acid methyl ester or analog thereof may then be isolated from the reaction mixture. The isolation may involve precipitation or crystallization of the threo-α-phenyl-α-(2-piperidinyl)acetic acid methyl ester or analog thereof.

In some embodiments, the supernatant remaining after precipitation of the threo-α-phenyl-α-(2-piperidinyl)acetic acid methyl ester or analog thereof may be further used in one or more subsequent synthetic processes. Thus, supernatant recovered from a first run of the process may be used in a second run of the process upon combining the supernatant with threo-α-phenyl-α-(2-piperidinyl)acetic acid, alcohol, acid and a water scavenger in a one-stage or two-stage process. Accordingly, the supernatants from one or more runs of the processes may be used in succeeding runs. This may result in a greater yield, a higher purity of the amino acid ester and/or a more efficient usage of the reaction components.

The threo-α-phenyl-α-(2-piperidinyl)acetic acid methyl ester or analog thereof prepared by the process above and isolated from the reaction mixture may be further purified by any suitable method such as, for example, by crystallization. For example, the compound may be dissolved in an appropriate solvent, such as ethanol, upon heating followed by cooling the solution to crystallize the compound. A threo-α-phenyl-α-(2-piperidinyl)acetic acid methyl ester may also be precipitated, e.g., in an amorphous form, using a similar method.

The process as described above produces the threo-α-phenyl-α-(2-piperidinyl)acetic acid methyl ester or analog thereof as the hydrochloride salt, however other pharmaceutically acceptable salts may be formed by any suitable method. For example, the hydrochloride salt may be converted to its free base form and then reacted with a suitable acid. The desired salt thus formed is then isolated. Representative salts include the hydrobromide, sulfate, bisulfate, phosphate, nitrate, acetate, valerate, oleate, palmitate, stearate, laurate, benzoate, lactate, phosphonate, tosylate, citrate, maleate, fumarate, succinate, tartrate, napthylate, mesylate, glucoheptonate, lactobionate, and laurylsulphonate salts and the like. In some instances, however, amino acid esters may be produced that are not salts.

The present invention provides several advantages over current methods for synthesizing threo-methylphenidate and its d-enantiomer (see, for example, U.S. Patent Application Publication No. 20060135777). In those methods, the carboxylic acids are converted into the corresponding acid chlorides by means of thionylchloride, and subsequently reacting these intermediates with an alcohol to generate the desired esters. The chlorination reaction with thionylchloride requires an additional aprotic solvent and evolves waste hydrogen chloride (HCl) gas and waste sulfurdioxide ($SO_2$) gas which typically requires additional processing. The present invention does not require an aprotic solvent and does not evolve $SO_2$ gas. The HCl gas can be recycled in the present invention and fewer reaction vessels are required to run the reaction—one for the reaction and one for collecting distillate and uses approximately one third the amount of solvent as the thionyl chloride process per kilogram of methylphenidate•HCl salt isolated.

Compounds made by the processes of the present invention, including where applicable their pharmaceutically acceptable salts, act as mild central nervous system stimulants. The compounds may be used in the treatment of attention-deficit disorder and attention-deficit hyperactivity disorder as well as other diseases and conditions benefiting from central nervous system stimulation.

The compounds made by the processes of the present invention and their pharmaceutically acceptable salts, may be administered via oral, transdermal (e.g., through the use of a patch), intranasal, sublingual, rectal, parenteral or topical routes. Oral and transdermal administration are preferred. These compounds are, most desirably, administered in dosages ranging from about 0.01 mg up to about 1500 mg per day, preferably from about 0.1 to about 300 mg per day in single or divided doses, although variations will necessarily occur depending upon the weight and condition of the subject being treated and the particular route of administration chosen. However, a dosage level that is in the range of about 0.001 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The compounds made by the processes of the present invention and their pharmaceutically acceptable salts may be administered alone or in combination with pharmaceutically acceptable carriers or diluents by any of the several routes previously indicated. More particularly, the compounds may be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

As various changes could be made in the above compounds, products and methods without departing from the scope of the invention, it is intended that all matter contained in the above description and in the examples given below, shall be interpreted as illustrative and not in a limiting sense.

EXAMPLES

Example 1

This example illustrates the synthesis of threo-methylphenidate by the process of the present invention.

Thirty grams of threo-α-phenyl-α-(2-piperidinyl)acetic acid containing 99.51% by weight of the threo-diastereomer and 0.49% by weight of the erythro-diastereomer were combined with 86.5 grams of methanolic HCl which contained 14.3% by weight of HCl (equivalent to 12.4 grams of HCl and 74.1 grams of methanol). The reaction mixture was heated to reflux at a maximum temperature of 68.5° C. for about 5 to 6 hours followed by addition of 41.1 grams of trimethyl orthoacetate. The reaction mixture was then heated to reflux at 60° C. to 63° C. for an additional period of about 3 to 4 hours. The threo-ester was isolated from the reaction liquid after partial distillation of the methanol and methyl acetate formed from the ortho ester. Isolation was achieved by lowering the temperature of the reaction liquid to <10° C. and recovering the precipitate. 24.7 grams of threo-methylphenidate was obtained for an isolated yield of 69.8%.

Examples 2-6

These examples illustrate various aspects of the synthesis of threo-methylphenidate by the process of the present invention as described below and summarized in Table 1.

Example 2 illustrates the process performed as in Example 1 except that the threo-methylphenidate was isolated from isopropyl alcohol after solvent exchange.

Example 3 illustrates the reaction in which the trimethyl orthoacetate was added at the start of the reaction.

Examples 4, 5 and 6 illustrate the reaction in absence of the water sequestrant, trimethyl orthoacetate, in which isolation was from methanol (Examples 4 and 5) or from isopropyl alcohol after solvent exchange (Example 6).

were found to be 0.10 and 0.17% when the product was isolated from methanol and isopropyl alcohol/methanol, respectively (Examples 1 and 2). In contrast to this, the impurity in products isolated from reactions in which trimethyl orthoacetate was absent ranged from 0.46 to 0.75% with esterification conversion at ≦95.5% (Examples 4-6).

TABLE 1

Threo-acid Esterification With and Without Trimethyl Orthoacetate

| PARAMETERS | EXAMPLE | | | | | |
|---|---|---|---|---|---|---|
| | 1 | 2 | 3 | 4 | 5 | 6 |
| TMOA Addition | after reaction[1] | after reaction[1] | at start | none | none | none |
| Solvent Distillation | yes[2] | yes[3] | No | no | no | yes[4] |
| Ester Isolated from | methanol | IPA/ methanol | methanol | methanol | Methanol | IPA/ methanol |
| Material Usage | | | | | | |
| Threo Acid (Grams) | 30.0 | 29.9 | 25.0 | 20.0 | 25.0 | 29.8 |
| Erythro Acid (wt %) | 0.49 | 0.67 | 0.47 | 0.41 | 0.47 | 0.51 |
| Methanolic HCl (grams) | 86.5 | 103.7 | 70.6 | 58.0 | 69.7 | 84.1 |
| HCl (wt %) | 14.3 | 14.4 | 14.6 | 10.9 | 14.6 | 14.7 |
| Water (wt %) | 0.8 | 0.7 | <0.05 | 2.8 | <0.05 | 0.5 |
| TMOA (grams) | 41.1 | 43.3 | 13.8 | none | None | none |
| Equivalents[5] | | | | | | |
| HCl | 2.5 | 3.0 | 2.5 | 1.9 | 2.4 | 2.5 |
| TMOA | 2.5 | 2.6 | 1.0 | 0.0 | 0.0 | 0.0 |
| Esterification | | | | | | |
| Total Time (hours)[6] | 9 | 9 | 15 | 10 | 9 | 5 |
| Maximum Reflux (° C.) | 68.5 | 69.4 | 65.5 | 68.2 | 69.2 | 69.2 |
| Conversion (%)[7] | 98.4 | 98.3 | 93.1 | 92.0 | 95.5 | 94.5 |
| Product Isolation | | | | | | |
| Concentration (wt %)[8] | 33.5 | 21.4 | 28.7 | 26.7 | 33.3 | 26.7 |
| Temperature (° C.) | <10 | <10 | <10 | <10 | <10 | 20 |
| Total (grams) | 24.7 | 34.3 | 13.1 | 10.0 | 13.9 | 31.9 |
| Isolated Yield (%) | 69.8 | 95.0 | 43.2 | 42.2 | 46.2 | 88.5 |
| Product Analysis (wt %) | | | | | | |
| Threo Acid | 0.10 | 0.17 | 0.94 | 0.75 | 0.46 | 0.51 |
| Erythro Isomer | 0.02 | 0.00 | 0.02 | 0.00 | 0.00 | 0.01 |
| Methylphenidate HCl | 99.4 | 99.4 | 98.1 | 98.8 | 99.1 | 99.0 |

[1]Trimethyl Orthoacetate (TMOA) added after 5 to 6 hours of heating.
[2]Methyl acetate and methanol partially distilled prior to isolation.
[3]Three solvent distillations and IPA additions prior to isolation.
[4]Two solvent distillations with intermediate IPA addition prior to isolation.
[5]Equivalents relative to initial threo and erythro acid charged.
[6]Total time at reflux before and after trimethyl orthoacetate addition (if any)
[7]Threo acid conversion based on crude product sample (area percent) analysis by HPLC.
[8]Concentration of methylphenidate HCl prior to isolation estimated by material balance.

The examples in Table 1 illustrate the increased conversion, yield and product purity obtained by adding trimethyl orthoacetate to the reaction, particularly when the threo-acid had been heated to reflux in methanolic HCl for several hours prior to the addition of the trimethyl orthoacetate. In the absence of trimethyl orthoacetate, the conversion of threo-acid to the threo-methylester was limited to ≦95.5% for reaction times up to 10 hours (Examples 4-6). The addition of one equivalent of trimethyl orthoacetate to the starting mixture reduced the reflux temperature by several degrees and threo acid conversion reached 93% only after 15 hours of reflux (Example 3). In comparison to this, conversion exceeded 98% when about 2½ equivalents of trimethyl orthoacetate were added after heating threo acid in methanolic HCl for at least 5 hours (Examples 1 and 2). This increase in conversion was accompanied by a substantial increase in product purity in which values for residual starting material Examples 7-9

These examples illustrate the improvement in yield resulting from recycling the supernatant and repeating the process for synthesis of threo-methylphenidate as described below and summarized in Table 2.

TABLE 2

Threo-acid Esterification with Trimethyl Orthoacetate and Supernatant Recycling[1]

| PARAMETER | EXAMPLE | | | |
|---|---|---|---|---|
| | 1 | 7 | 8 | 9 |
| Material Usage | | | | |
| Threo Acid (grams) | 30.0 | 21.6 | 22.6 | 23.4 |
| Erythro Acid (wt %) | 0.49 | 0.49 | 0.49 | 0.51 |

TABLE 2-continued

Threo-acid Esterification with Trimethyl Orthoacetate and Supernatant Recycling[1]

| PARAMETER | EXAMPLE | | | |
|---|---|---|---|---|
| | 1 | 7 | 8 | 9 |
| Methanolic HCl (grams) | 86.5 | 44.6 | 82.3 | 78.6 |
| HCl (wt %) | 14.3 | 14.1 | 13.8 | 15.0 |
| Water (wt %) | 0.8 | 0.9 | 1.2 | 0.4 |
| Recycle Liquor (grams) | none | 78.9 | 60.2 | 67.6 |
| Water (wt %) | na | 1.2 | 0.7 | 1.1 |
| Threo Acid (wt %) | na | 0.2 | 2.3 | 0.2 |
| Erythro Isomer (wt %) | na | 0.2 | 0.3 | 0.5 |
| Methylphenidate (wt %) | na | 12.5 | 12.9 | 10.0 |
| TMOA (grams) | 41.1 | 29.9 | 40.1 | 38.2 |
| Equivalents[2] | | | | |
| HCl | 2.5 | 1.5 | 2.5 | 2.6 |
| TMOA | 2.5 | 1.8 | 2.4 | 2.4 |
| Esterification | | | | |
| Time (hours)[3] | 9 | 21.5 | 8 | 7 |
| Maximum Reflux (° C.) | 68.5 | 67.2 | 67.8 | 67.1 |
| Conversion (%)[4] | 98.4 | 91.7 | 97.9 | 98.5 |
| Product Isolation | | | | |
| Concentration (wt %)[5] | 33.5 | 41.3 | 34.4 | 32.6 |
| Total (grams) | 24.7 | 21.8 | 25.8 | 25.6 |
| Isolated Yield (%) | 69.8 | 63.7 | 70.7 | 72.7 |
| Product Analysis (wt %) | | | | |
| Threo Acid | 0.10 | 0.73 | 0.10 | 0.06 |
| Erythro Isomer | 0.02 | 0.03 | 0.03 | 0.05 |
| Methylphenidate HCl | 99.4 | 100.7 | 99.7 | 101.6 |

[1]In each run, the trimethyl orthoacetate was added after 5-20 hours of reflux; methyl acetate and methanol were partially distilled prior to isolation; and the threo-methylester was isolated from methanol at <10° C.
[2]Equivalents relative to total threo/erythro acid and ester charged.
[3]Total time of reflux before and after trimethyl orthoester addition.
[4]Threo-acid conversion base on crude product sample (area percent) analysis by HPLC.
[5]Concentration of methylphenidate HCl prior to isolation estimated by material balance.

The Examples 7-9 in Table 2 illustrate the effect of recycling of liquors. As seen in the table, recycling improves the yield when the threo-methylester was isolated directly from methanol. The four runs in Examples 1 and 7-9 were carried out sequentially, with liquors from each run recycled to the next. Three of the runs (Examples 1, 8 and 9) used about 2% equivalents each of HCl and trimethyl orthoacetate and this resulted in threo-acid conversions of 97.9 to 98.5% after 7 to 9 hours at reflux. After partially distilling methyl acetate and methanol from the reaction mixtures, threo-methylphenidate HCl containing ≦0.10 wt % threo-acid was isolated in these runs, at yields of 69.8 to 72.7% (see Examples 1, 8 and 9). The quantities of HCl and trimethyl orthoacetate were reduced in the second run (Example 7), which resulted in a lower conversion and yield, and a higher threo-acid impurity in the isolated product. In spite of this, the only qualitative difference between the first run (Example 1) and the fourth run (Example 9) was a small increase in the erythro isomer impurity (from 0.02 to 0.05%). The cumulative yield from these four batches was 84.5%. At a constant 70% per-batch yield, the cumulative yield from a four-batch series is about 90%.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description, which do not depart from the spirit or scope of the present inventive discovery. Such modifications are also intended to fall within the scope of the appended claims.

All references cited in this specification are hereby incorporated by reference. The discussion of the references herein is intended merely to summarize the assertions made by their authors and no admission is made that any reference constitutes prior art relevant to patentability. Applicant reserves the right to challenge the accuracy and pertinency of the cited references.

What is claimed is:

1. A synthetic esterification process comprising:
(i) reacting
(a) an amino acid of Formula I:

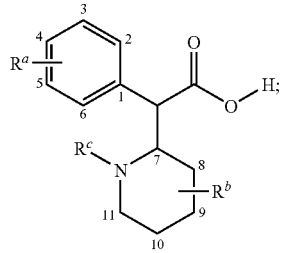

Formula I wherein $R^a$ is a substituent at one or more of carbons 2, 3, 4, 5 and 6 of the phenyl ring, wherein the substituent is independently selected from the group consisting of hydrogen, alkyl, alkoxy, haloalkyl, haloalkoxy, hydroxyalkyl, alkoxyalkyl, halogen and —$NR_mR_n$, wherein $R_m$ and $R_n$ are independently selected from the group consisting of hydrogen, alkyl, haloalkyl and alkoxyalkyl;

wherein $R^b$ is a substituent at one or more of carbons 7, 8, 9, 10 and 11 of the piperidine ring, wherein the substituent is independently selected from the group consisting of hydrogen, oxo, alkyl, alkoxy, haloalkyl, haloalkoxy, hydroxyalkyl, alkoxyalkyl and halogen; and wherein $R^c$ is selected from the group consisting of hydrogen, alkyl, haloalkyl, aralkyl, cycloalkylalkyl, hydroxyalkyl, alkoxyalkyl, and

wherein $R^t$ is selected from the group consisting of alkyl, alkoxy, cycloalkyl, cycloalkylalkyl, aralalkoxy and aralkyl;

with (b) an alcohol of formula $R^y$—OH, wherein $R^y$ is selected from the group consisting of alkyl, haloalkyl, cycloalkyl, cycloalkylalkyl, aryl, aralkyl, heteroaryl, and heteroaralkyl;

in the presence of
(c) an acid;
and
(d) a water sequestrant
to produce a reaction mixture containing an amino acid ester of Formula II

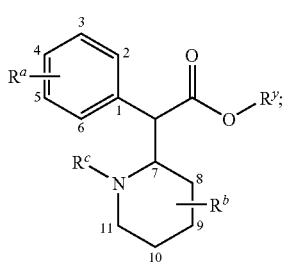

Formula II and (ii) isolating the amino acid ester of Formula II or a pharmaceutically acceptable salt thereof.

2. The process of claim 1, wherein the amino acid is ritalinic acid.

3. The process of claim 1, wherein the water sequestrant is an orthoester of the formula $R^xC(OR^y)_3$, wherein $R^x$ is hydrogen or alkyl and $R^y$ is as previously defined; and the acid is selected from the group consisting of methanesulfonic acid, p-toluenesulfonic acid, hydrochloric acid, hydrobromic acid, sulfuric acid, and phosphoric acid.

4. The process of claim 1, wherein the water sequestrant is $CH_3C(OCH_3)_3$.

5. The process of claim 1, wherein the water sequestrant is employed in an amount from about 0.5 to about 4 molar equivalents to that of the amino acid; the alcohol is employed in an amount from about 5 to about 50 molar equivalents to that of the amino acid of Formula I; and the acid is employed in an amount from about 0.5 to about 4 molar equivalents to that of the amino acid of Formula I.

6. The process of claim 1, wherein the alcohol is methanol.

7. The process of claim 1, wherein the reaction is carried out from about 25° C. to about 150° C.

8. The process of claim 1, wherein the water sequestrant is added to the reaction mixture prior to complete conversion to the amino acid ester of Formula II.

9. The process of claim 1, wherein isolating comprises precipitating or crystallizing the amino acid ester of Formula II or a pharmaceutically acceptable salt thereof from the mixture.

10. The process of claim 9, further comprising capturing supernatant remaining after precipitating or crystallizing the amino acid ester of Formula II or a pharmaceutically acceptable salt thereof; and repeating (i) through (ii) one or more times utilizing captured supernatant.

11. A process for preparing threo-α-phenyl-α-(2-piperidinyl)acetic acid methyl ester, the process comprising (i) reacting threo-α-phenyl-α-(2-piperidinyl)acetic acid with methanol in the presence of a water sequestrant and an acid; and (ii) isolating the threo-α-phenyl-α-(2-piperidinyl)acetic acid methyl ester or a pharmaceutically acceptable salt thereof.

12. The process of claim 11, wherein the water sequestrant is an orthoester of formula $R^xC(OCH_3)_3$, wherein $R^x$ is hydrogen or alkyl.

13. The process of claim 11, wherein the water sequestrant is $CH_3C(OCH_3)_3$.

14. The process of claim 11, wherein the water sequestrant is employed in an amount from about 0.5 to about 4 molar equivalents to that of threo-α-phenyl-α-(2-piperidinyl)acetic acid; the methanol is employed in an amount from about 5 to about 50 molar equivalents to that of threo-α-phenyl-α-(2-piperidinyl)acetic acid; and the acid is employed in an amount from about 0.5 to about 4 molar equivalents to that of threo-α-phenyl-α-(2-piperidinyl)acetic acid.

15. The process of claim 11, wherein the acid is selected from the group consisting of methanesulfonic acid, p-toluenesulfonic acid, hydrochloric acid, hydrobromic acid, sulfuric acid, and phosphoric acid.

16. The process of claim 11, wherein the reaction is carried out from about 0° C. to about 200° C.

17. The process of claim 11, wherein the reaction is carried out from about 25° C. to about 150° C.

18. The process of claim 11, wherein the reaction is carried out from about 50° C. to about 100° C.

19. The process of claim 11, wherein isolating threo-α-phenyl-α-(2-piperidinyl)acetic acid methyl ester or a pharmaceutically acceptable salt thereof is by precipitation or crystallization from the reaction mixture.

20. The process of claim 19, further comprising capturing supernatant remaining after precipitation or crystallization of the threo-α-phenyl-α-(2-piperidinyl)acetic acid methyl ester or a pharmaceutically acceptable salt thereof; and repeating (i) through (ii) one or more times utilizing captured supernatant.

* * * * *